United States Patent [19]

Eilerman et al.

[11] 4,428,870

[45] Jan. 31, 1984

[54] PERFUME COMPOSITION CONTAINING PHENYLETHYNYL CARBINOLS

[75] Inventors: Robert G. Eilerman, Merrick, N.Y.; Brian J. Willis, Ramsey; John M. Yurecko, Jr., Bayonne, both of N.J.

[73] Assignee: Fritzsche Dodge & Olcott Inc., New York, N.Y.

[21] Appl. No.: 337,251

[22] Filed: Jan. 5, 1982

[51] Int. Cl.[3] ........................... A61K 7/46; C11B 9/00

[52] U.S. Cl. ................................................ 252/522 R

[58] Field of Search .................... 252/522 R; 568/813; 424/64, 65

[56] References Cited

U.S. PATENT DOCUMENTS

| | | | |
|---|---|---|---|
| 2,693,489 | 11/1954 | Kleinschmidt | 568/813 X |
| 4,088,681 | 5/1978 | Baumann et al. | 252/522 R X |
| 4,206,090 | 6/1980 | Schmitt | 252/522 R |
| 4,210,610 | 7/1980 | Sabourin et al. | 568/813 X |
| 4,223,172 | 9/1980 | Sabourin et al. | 568/813 X |

OTHER PUBLICATIONS

Arctander, Perfume and Flavor Chemicals, Steffen Arctander, N.J., vol. I #618 (1969).

Arctander, Perfume and Flavor Chemicals, Steffen Arctander, N.J., vol. II, #'s 2643, 2494, 2589 (1969).

Smissman et al., J.A.C.S. 78, pp. 3395-3400 (1956).

*Primary Examiner*—Helen M. S. Sneed

*Attorney, Agent, or Firm*—Cooper, Dunham, Clark, Griffin & Moran

[57] ABSTRACT

The invention discloses perfume compositions containing one or more phenylethynyl carbinol compounds along with conventional perfume ingredients. The phenylethynyl carbinol compounds have the formula:

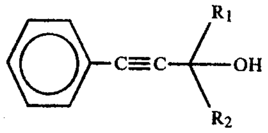

wherein $R_1$ and $R_2$ is the same or different lower alkyl.

6 Claims, No Drawings

PERFUME COMPOSITION CONTAINING PHENYLETHYNYL CARBINOLS

FIELD OF THE INVENTION

This invention is concerned with the production of novel perfumes and perfumed articles containing phenylethynyl carbinol compounds.

BACKGROUND OF THE INVENTION

There is a continual search for new and inexpensive chemicals which can be utilized to modify, enhance, or otherwise improve the organoleptic properties of consumable products.

Although many acetylenic compounds are found naturally, the use of this class of compounds in perfumery has been limited. Arctander in "Perfume and Flavor Chemicals", 1969, describes the ester methyl 2-nonynoate, commonly known as "methyl heptine carbonate", as well as related acetylenes. U.S. Pat. No. 3,268,594 discloses compounds having the structure:

$$CH_3(CH_2)_nC{\equiv}CCH(OCH_3)_2$$

which are useful as perfumery ingredients.

SUMMARY OF THE INVENTION

The present invention provides for perfume compositions having new and improved organoleptic properties.

Accordingly, it is an object of the invention to provide novel perfume compositions and perfumed articles which incorporate one or more phenylethynyl carbinol compounds into their fragrance formulas. Broadly, this invention provides for a perfume composition comprising:

a. one or more phenylethynyl carbinols having the structure:

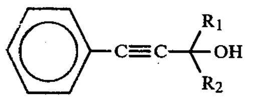

Formula I wherein $R_1$ and $R_2$ is the same or different lower alkyl in an amount sufficient to impart fragrance thereto; and b. conventional perfume ingredients.

DETAILED DESCRIPTION OF THE INVENTION

The present invention provides for the production of novel perfumes and perfumed articles through the use of sufficient amounts of one or more of the phenylethynyl carbinols having the general formula presented hereinabove. Alkyl groups suitable for use in this invention perferably contain from 1 to 6 carbon atoms, most preferably from 1 to 4 carbon atoms. The alkyl groups may be straight chained or branched, cyclic or acyclic. The alkyls are perferably methyl, ethyl and isopropyl. The phenylethynyl carbinols preferably contain between 11 and about 16 carbon atoms.

Table I hereinafter illustrates some preferred compounds of Formula I which are characterized by odor notes.

EXAMPLES OF COMPOUNDS OF FORMULA I

| | |
|---|---|
| 3-Methyl-1-phenyl-1-butyn-3-ol<br>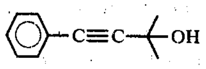 | green, floral |
| 3-Methyl-1-phenyl-1-pentyn-3-ol<br>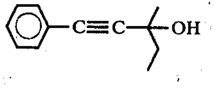 | rosey, floral muguet-like |
| 3-Ethyl-1-phenyl-1-pentyn-3-ol<br>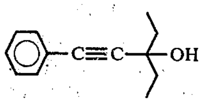 | fresh, rosey |
| 3,4-Dimethyl-phenyl-1-pentyn-3-ol<br>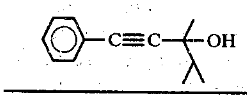 | sweet, floral slightly rosey |

Compounds of the present invention may be prepared in accordance with known technology by reacting phenylacetylene with the appropriate ketone as illustrated in accompanying Scheme I.

Scheme I

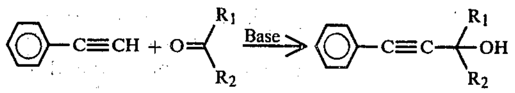

Such procedures are reported by Smissman et al., in the Journal of the American Chemical Society, Vol. 78, pp. 3395–3400 (1956) and are incorporated here by reference.

The phenylethynyl carbinols of the present invention have been found to possess distinctive green, floral, rosey, muguet, slightly balsamic odors which render them useful in fine fragrances as well as perfumed products such as soaps, detergents, deodorants, cosmetic preparations and the like.

One or more of the phenylethynyl carbinols of this invention and auxiliary perfume ingredients, for example, alcohols, aldehydes, ketones, nitriles, esters and essential oils, may be admixed so that the combined odors of the individual components produce a desired fragrance. Such perfume compositions are carefully balanced, harmonious blends of essential oils, aroma chemicals, resinoids and other extracts of natural odorous materials. Each perfume ingredient imparts its own characteristic effect to the composition. Thus, one or more of the phenylethynyl carbinols of the invention can be employed to impart novel characteristics into fragrance compositions.

Such perfume compositions may contain between about 0.001 and about 80 weight percent of any one or more of the phenylethynyl carbinols of this invention. Ordinarily, at least about 0.001 weight percent of the phenylethynyl carbinol is required to impart significant odor characteristics. Amounts of phenylethynyl compounds in the range of from about 1 to about 60 weight percent are preferred. The phenylethynyl carbinols of this invention may be formulated into concentrates containing from about 1 to about 60 weight percent of the compound in an appropriate solvent. Such concentrates are then employed to formulate products such as colognes, soaps, etc., wherein the concentration of the compounds of this invention can be in the range of from about 0.001 to 7 weight percent, depending upon the final product. For example, the concentration of the compounds of this invention will be of the order of about 0.001 to about 0.1 weight percent in detergents, and of the order of about 0.1 to about 7 weight percent in perfumes and colognes.

The phenylethynyl carbinols of this invention are useful as olfactory components of perfume compositions for detergents and soaps, space odorants and deodorants, perfumes, colognes, toilet water, bath preparations such as bath oils and bath solids, hair preparations such as lacquers, brilliantines, pomades and shampoos, cosmetic preparations such as creams, deodorants, hand lotions and sunscreens, powders such as talcs, dusting powders and face powders, and the like.

The following examples are set forth herein to illustrate the preferred method of synthesis of the compounds of this invention. In addition, examples are included which demonstrate their use in fragrance compositions. These examples are intended only to illustrate the preferred embodiments of this invention and are in no way meant to limit the scope thereof.

EXAMPLE 1

Preparation of 3-Methyl-1-phenyl-1-pentyn-3-ol

Phenylacetylene (500 g, 4.2 mol) was added to a mixture of potassium hydroxide flake (290 g) and toluene (3 L). 2-Butanone (425 g, 5.9 mol) was added over 45 minutes keeping the temperature below 30° C. with periodic cooling and the resulting mixture agitated for 20 h at room temperature. Water (1 L) was added, the toluene solution washed until neutral, the solvent evaporated, and the residue distilled to give 517 g (71% yield) of 3-methyl-1-phenyl-1-pentyn-3-ol; bp 107°-110° C./3 mm; IR (film) 3400, 1150, 1000, 920 $cm^{-1}$; NMR ($CDCl_3$) 1.1 (3H, t), 1.6 (3H, s), 1.8 (2H, q), 2.2 (1H, s), 7.2-7.6 (5.H, m) δ; MS (m/e) 174, 156, 145, 43.

EXAMPLE 2

Preparation of 3-Methyl-1-phenyl-1-butyn-3-ol

The procedure outlined in Example 1 was followed using acetone and resulted in the isolation of 403 g (60% yield) of 3-methyl-1-phenyl-1-butyn-3-ol: bp 101° C./3 mm [mp 52°-53° C./from hexane]; IR (film) 3400, 1150, 960, 910 $cm^{-1}$; NMR ($CDCl_3$) 1.6 (6H, s), 2.2 (1H, s), 7.2-7.5 (5H, m) δ; MS (m/e) 160, 142, 145, 43.

EXAMPLE 3

Preparation of 3-Ethyl-1-phenyl-1-pentyn-3-ol

The procedure outlined in Example 1 was followed using 3-pentanone and resulted in the isolation of 568 g (72% yield) of 3-ethyl-1-phenyl-1-pentyn-3-ol: bp 117°-118° C./3 mm; IR (film) 3400, 1310, 1130, 950 $cm^{-1}$; NMR ($CDCl_3$) 1.1 (6H, t), 1.8 (4H, q), 2.1 (1H, s), 7.2-7.6 (5H, m) δ; MS (m/e) 188, 160, 159, 57.

EXAMPLE 4

Preparation of 3,4-Dimethyl-1-phenyl-1-pentyn-3-ol

The procedure outlined in Example 1 was followed using 3-methyl-2-butanone and resulted in the isolation of 458 g (58% yield) of 3,4-dimethyl-1-phenyl-1-pentyn-3-ol: bp 113°-115° C./3 mm; IR (film) 3400, 1100, 1060, 910 $cm^{-1}$; NMR ($CDCl_3$) 1.1 (6H, 2d), 1.5 (3H, s) 1.6-2.0 (1H, m), 2.2 (1H, s), 7.2-7.6 (5H, m) δ; MS (m/e) 188, 160, 145, 43.

EXAMPLE 5

The following illustrates the use of the phenylethynyl carbinols in a perfume composition of the muguet type.

BASE COMPOSITION

| Component | Parts by weight |
|---|---|
| cis-3-Hexenol | 1.0 |
| Tonalide | 3.0 |
| Indole (10% in DEP) | 3.0 |
| Citral quenched | 5.0 |
| Alpha Ionone | 7.0 |
| Nerolidol | 8.0 |
| Citronellyl formate | 8.5 |
| Geranyl acetate | 9.5 |
| Citronellyl propionate | 20.0 |
| Jasmin absolute B | 25.0 |
| Linalool synthetic | 45.0 |
| Terpineol | 65.0 |
| Phenylethyl alcohol | 70.0 |
| Hydroxycitronellal | 100.0 |
| Benzyl alcohol | 200.0 |
| | 570.0 |

MODIFYING INGREDIENTS

| Component | Parts by weight A | B | C | D |
|---|---|---|---|---|
| Geraniol | 200 | — | — | — |
| Laevo citronellol | 230 | — | — | — |
| 3-Methyl-1-phenyl-1-pentyn-3-ol | — | 430 | — | — |
| 3-Ethyl-1-phenyl-1-pentyn-3-ol | — | — | 400 | — |
| 3,4-Dimethyl-1-phenyl-1-pentyn-3-ol | — | — | — | 370 |
| Diethyl phthalate | — | — | 30 | 60 |
| Base | 570 | 570 | 570 | 570 |
| | 1000 | 1000 | 1000 | 1000 |

When varying amounts of the phenylethynyl carbinols (formulations B, C and D) were mixed with the base as indicated, the character of the finished products was more rounded and esthetic as evaluated in both the freshly blottered and on dry out, than compositions A with the rose alcohols normally used.

EXAMPLE 6

The following illustrates the use of several phenylethynyl carbinols in the preparation of a substitute Rose absolute.

BASE COMPOSITION

| Component | Parts by weight |
|---|---|
| Phenylacetic acid | 2 |
| Rosetone | 4 |
| Benzyl isoeugenol | 10 |
| Oakmoss absolute | 4 |
| Dimethylbenzylcarbinyl acetate | 20 |
| Guaiacwood acetate | 20 |
| Honey base | 10 |
| Undecylenic alcohol | 2 |
| Aldehyde $C_9$ (10% in DEP) | 15 |
| Aldehyde undecylenic (10% in DEP) | 20 |
| Alcohol $C_9$ | 2 |
| Mimosa absolute | 2 |
| Oil Chamomile blue | 1 |

-continued

| BASE COMPOSITION | |
|---|---|
| Component | Parts by weight |
| Methyl octine carbonate (1% in DEP) | 10 |
| Penylacetaldehyde dimethyl acetal | 9 |
| Costus | 5 |
| Isobutylphenyl acetate | 12 |
| Alpha Irisone white extra | 25 |
| Oil Geranium bourbon | 19 |
| Oil Ceranium Maroc selection | 40 |
| Phenylethyl acetate | 12 |
| Citronellyl formate | 40 |
| Dibutylsulfide (1% in DEP). | 4 |
| Geranyl acetate | 50 |
| Phenylethyl alcohol | 90 |
| 2-trans-6-cis-Nonadienal (5% in DEP) | 2 |
| | 430 |

| MODIFYING INGREDIENTS | | | | | |
|---|---|---|---|---|---|
| | Parts by weight | | | | |
| Component | A | B | C | D | E |
| Geraniol ex Palmarosa | 270 | — | — | — | — |
| Laevo citronellol | 300 | — | — | — | — |
| 3-Methyl-1-phenyl-1-pentyn-3-ol | — | 570 | — | — | — |
| 3-Ethyl-1-phenyl-1-pentyn-3-ol | — | — | 530 | — | — |
| 3,4-Dimethyl-1-phenyl-1-pentyn-3-ol | — | — | — | 500 | — |
| 3-Methyl-1-phenyl-1-butyn-3-ol | — | — | — | — | 570 |
| Diethyl phthalate | — | — | 40 | 70 | — |
| Base | 430 | 430 | 430 | 430 | 430 |
| | 1000 | 1000 | 1000 | 1000 | 1000 |

When the rose absolute is made up with the varying amounts of phenylethynyl carbinols as indicated above (formulations B, C, D and E), the characteristics of the finished products are more esthetic and better balanced than the one made with the rose alcohols (example A) normally used.

We claim:

1. A perfume composition comprising: a. one or more phenylethynyl carbinols having the structure:

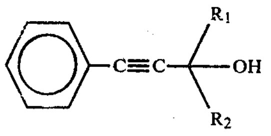

wherein $R_1$ and $R_2$ is the same or different lower alkyl in an amount sufficient to impart fragrance thereto.

2. The perfume composition of claim 1 wherein the phenylethynyl carbinol compounds are employed in an amount between about 0.001 and about 80 weight percent.

3. The perfume composition of claim 1 wherein the phenylethynyl carbinol has the structure:

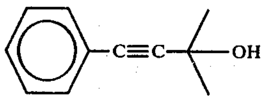

4. The perfume composition of claim 1 wherein the phenylethynyl carbinol has the structure:

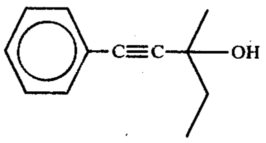

5. The perfume composition of claim 1 wherein the phenylethynyl carbinol has the structure:

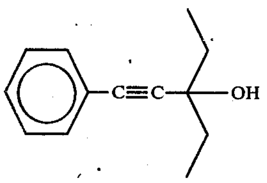

6. The perfume composition of claim 1 wherein the phenylethynyl carbinol has the structure:

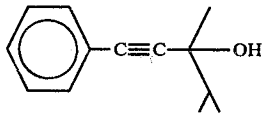

* * * * *